United States Patent [19]

Haber et al.

[11] Patent Number: 5,300,038

[45] Date of Patent: Apr. 5, 1994

[54] SAFETY SYRINGE WITH OFF-AXIS NEEDLE CANNULA

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 56,850

[22] Filed: Apr. 30, 1993

[51] Int. Cl.⁵ ............................................. A61M 5/00
[52] U.S. Cl. .................................. 604/187; 604/198; 604/272
[58] Field of Search ............... 604/198, 187, 110, 272, 604/191, 263

[56] References Cited

U.S. PATENT DOCUMENTS

| | | | |
|---|---|---|---|
| 4,150,669 | 4/1979 | Latorre | 604/191 X |
| 4,512,768 | 4/1985 | Rangaswamy | 604/272 X |
| 4,573,976 | 3/1986 | Sampson . | |
| 4,734,261 | 3/1988 | Koizumi et al. | 604/191 X |
| 4,834,717 | 5/1989 | Haber . | |
| 4,900,307 | 2/1990 | Kulli . | |
| 4,927,414 | 5/1990 | Kulli . | |
| 4,941,883 | 7/1990 | Venturini . | |
| 4,966,593 | 10/1990 | Lennox . | |
| 5,013,301 | 5/1991 | Marotta, Jr. . | |
| 5,052,403 | 10/1991 | Haber . | |
| 5,064,419 | 11/1991 | Gaarde . | |
| 5,085,640 | 2/1992 | Gibbs . | |
| 5,147,323 | 9/1992 | Haber . | |

FOREIGN PATENT DOCUMENTS 0287950 10/1988 European Pat. Off. .

Primary Examiner—John D. Yasko
Attorney, Agent, or Firm—Townsend and Townsend Khourie and Crew

[57] ABSTRACT

A syringe (2), of the type having a barrel (4) with a plunger (6) disposed within the bore of the barrel, includes two needle assemblies (22) housed within needle assembly guides (14) positioned along the exterior (16) of the syringe barrel. Each needle assembly guide provides a path along which the needle assembly moves, between an extended position, with the needle exposed, and a retracted position, with the needle encompassed by the needle guide. A flow path (36, 44) exists between the interior (46) of the syringe barrel and each needle assembly when each needle assembly is in the extended position. The use of two needles allows one needle to be used to aspirate the liquid pharmaceutical into the syringe and the other, unused needle to be used to give the injection. Each needle assembly is irreversibly locked (54, 60) when moved into the retracted position to prevent syringe reuse.

13 Claims, 5 Drawing Sheets

SAFETY SYRINGE WITH OFF-AXIS NEEDLE CANNULA

CROSS REFERENCE TO RELATED APPLICATION

This application is related to U.S. Ser. No. 07/682,058 filed Apr. 8, 1991 which is herein incorporated by reference.

BACKGROUND OF THE INVENTION

Syringes are widely used for the administration of drugs or other substances to, or for the withdrawal of fluids from, a body. Syringes are also used for a variety of health industry and other purposes as well. Typically, a syringe includes a barrel and a plunger. The plunger is reciprocally disposed within the barrel, with the plunger protruding from the proximal end of the barrel throughout its range of movement. To utilize the syringe a needle will generally be attached to the distal end of the syringe barrel, the needle being coaxial with the central axis of the barrel. The syringe may be provided with the needle pre-placed in this location, with a protective cap or sheath covering the needle. Alternatively, and more commonly, a needle with an associated sheath is attached to the distal end of a syringe barrel prior to use.

Generally, the syringe barrel and needle sheath are mass produced from a low cost material, such as polypropylene, by a cost-efficient method such as injection molding. The needle is made of a suitable material, such as 304 stainless steel.

When administering a medicine the empty syringe is often filled from a vial containing the medicine. Medicine vials usually have a membrane covering the liquid opening. The needle is used to pierce the membrane to draw the medicine into the syringe.

A problem with drawing medicine from a vial is that the needle can be dulled when piercing the membrane. The dull needle can cause obvious problems when used for injecting the medicine into a patient.

One known solution to the problem is to remove the dulled needle and replace it with a fresh needle. This practice is, however, time consuming and also requires a supply of fresh needles. Furthermore, the dull needles are discarded individually presenting another possible hazard.

Subsequent to use the syringe needle will often be recapped and discarded in a suitable disposal container. In some settings the needle may be clipped prior to recapping, in an effort to preclude any illicit use of the needle after its disposal; however, clipping can release toxic and/or infectious aerosolization mists.

For many applications a syringe with a coaxial needle will suffice. However, there are numerous situations in which this embodiment presents significant obstacles to the effective use of the syringe. The typical syringe with a coaxial needle may have limited use when administering fluids intravenously, or particularly subcutaneously. The foregoing problems are exacerbated when larger volumes of fluid, and consequently larger diameter syringe barrels, are utilized.

Furthermore, very serious, even life threatening, problems may be associated with the attachment, but more particularly with the removal, of a needle from such a syringe. The problems associated with the recapping and disposal of previously-used syringe needles are also severe. In the medical industry an exceptionally high percentage of job-related needle sticks occur during the process of needle recapping. Such needle sticks may serve as a mode for the spread of infectious disease, and are accordingly of great concern. The clipping procedure may also lead to needle sticks and/or toxic or infectious aerosolization exposure; if the syringe barrel is not also clipped it may be illicitly used once a functional needle is obtained.

SUMMARY OF THE INVENTION

The present invention is directed to a safety syringe having two primary features: two needles are positioned along opposite sides of the barrel, rather than coaxially with the barrel, and the needles are retractable needles which are irreversibly locked into a safe, post-use, retracted position in a simple and effective manner.

The syringe is of the type having a barrel with a plunger disposed within the bore of the barrel. The syringe includes two needle assemblies housed within needle assembly guides, the needle assembly guides preferably being positioned along opposite sides of the exterior of the syringe barrel. Each needle assembly guide provides a path along which the needle assembly moves between an extended position, with the needle exposed, and a retracted position, with the needle encompassed by the needle guide. A flow path exists between the interior of the syringe barrel and each needle assembly when each needle assembly is in its extended position. Additionally, the needle assembly can be locked in the retracted position to prevent syringe reuse.

An advantage of the invention is that by providing the needle offset from the axis of the barrel, certain procedures, such as administering fluids intravenously or subcutaneously, is made easier. The radial offset reduces the angle of incidence between the needle cannula axis and the blood vessel axis or tissue layer plane. Also, radially offset positioning permits the needle to be retracted and extended without interfering with the movement of the plunger, thus making for a simple, compact safety syringe.

A further advantage of the invention is that one of the needles can be used to pierce a vial membrane and the other needle, which remains sharp, can be used for the injection. Providing a second needle eliminates the need to remove and change the needle used to pierce the vial membrane when a sharp needle is desired for the injection.

Other features and advantages of the invention will appear from the following description in which the preferred embodiment has been set forth in detail in conjunction with the accompanying drawings.

DESCRIPTION OF THE PREFERRED EMBODIMENT

Figure 1:
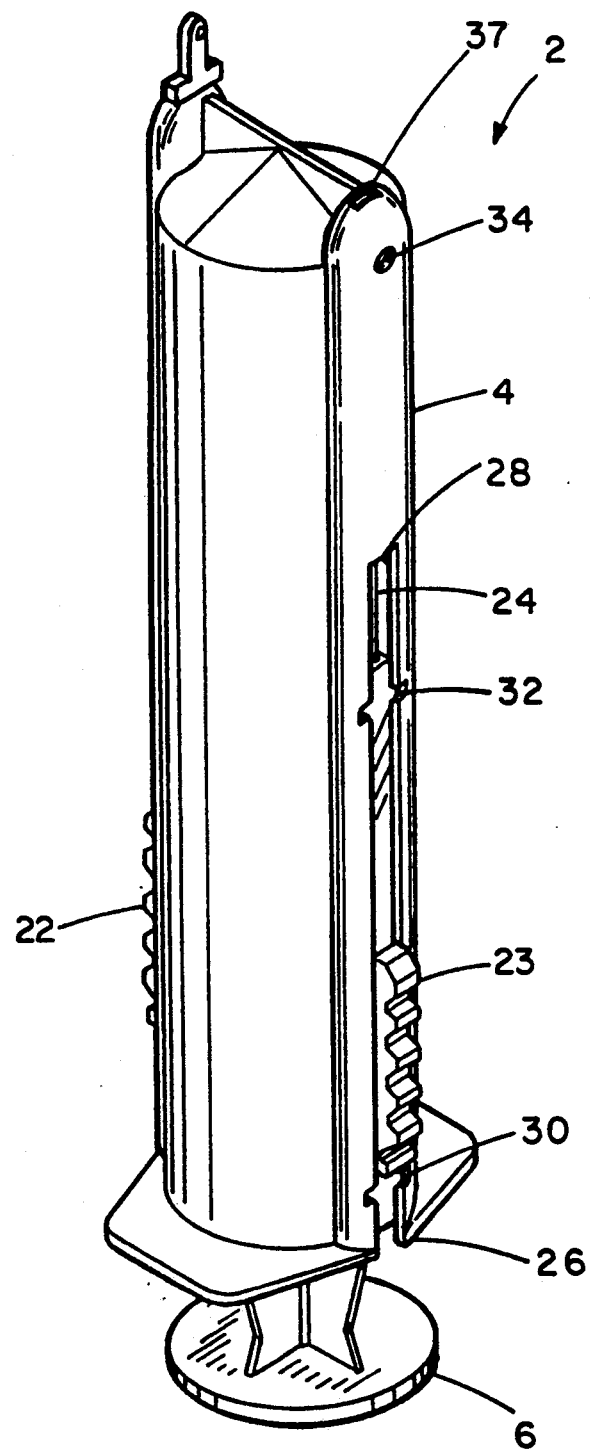
FIG. 1 is an isometric view of a syringe made according to the invention in a pre-use condition.
Figure 2:
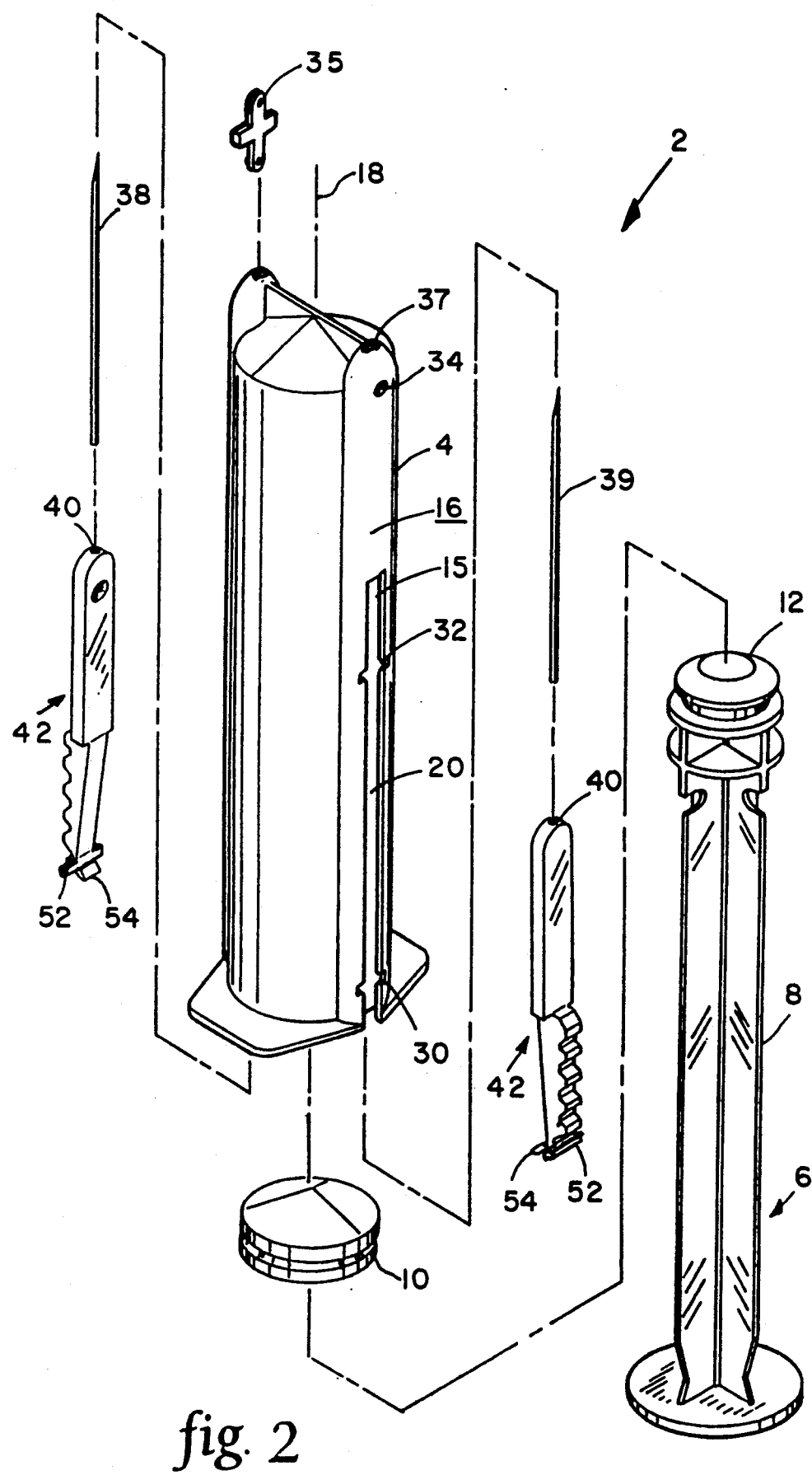
FIG. 2 is an exploded isometric view of the syringe.

FIGS. 1 and 2 illustrate a syringe 2 according to the invention. The syringe 2 includes a barrel 4 and a plunger 6. Plunger 6 includes a stem 8 and an elastomeric piston 10 which fits over the head 12 of stem 8 (FIG. 2).

Figure 3:
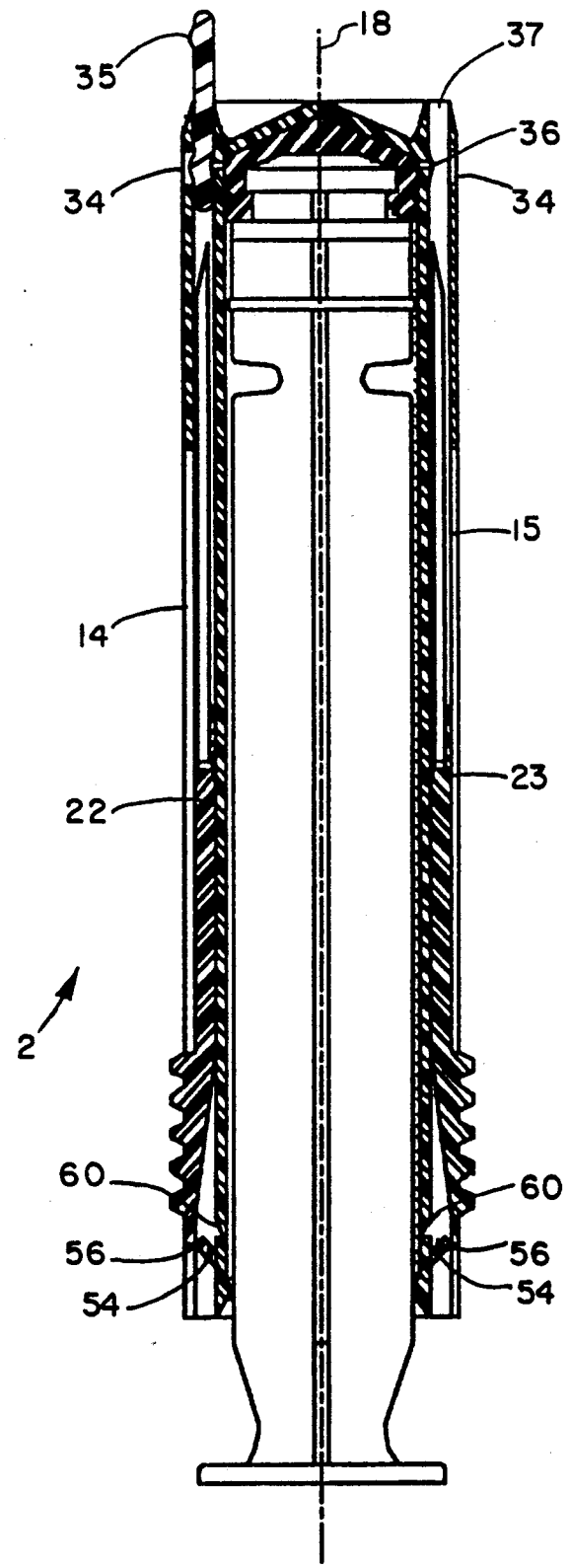
FIG. 3 is a front elevation cross-sectional view with the plunger fully inserted into the barrel and both needle assemblies in their pre-use, retracted positions.

The syringe includes first and second needle assembly guides 14, 15 each having an interior 20 and housing first and second needle assemblies 22, 23 respectively (FIGS. 2 and 3). Guides 14, 15 are each formed as a one-piece molded extension of barrel 4 positioned along the outside or exterior 16 of barrel 4. Barrel 4, guides 14, 15 and stem 8 are preferably clear and made of a medically compatible material, such as polypropylene. Guides 14, 15 are positioned parallel to but radially offset of the axis 18 of barrel 4.

Guides 14, 15 each include a longitudinally extending slot 24 extending from the proximal end 26 of barrel 4 to a position 28 along barrel 4. Slot 24 includes a pair of cutouts 30, 32 configured to temporarily secure needle assemblies 22, 23 in the pre-use, retracted positions of FIG. 3 and the in-use, extended position as discussed below. Guides 14, 15 each includes an access opening 34 overlying a port 36 (FIGS. 4, 4A) formed in barrel 4; openings 34 permit ports 36 to be molded through the wall of barrel 4.

The first and second needle assemblies 22, 23 include first and second hollow needles 38, 39, respectively, each mounted to the distal end 40 of a needle mount 42. Needle mount 42 is sized to slide within interior 20 of guides 14. As seen best in FIG. 4A, needle mount 42 includes an opening 44 which fluidly couples the interior of first hollow needle 38 with port 36 when needle assembly 22 is in extended position of FIG. 4. Port 36 and opening 44 create a first flow path from a distal, variable volume region 46 (FIG. 4), defined within barrel 4, and first hollow needle 38. Second needle 39 and the adjoining port 36, opening 44, and variable volume region 46 similarly define a second flow path. As can be seen best in FIG. 4A, the abutting surfaces 47, 48, which surround opening 44 and port 36, have complementary curved shapes to provide a good seal along the flow path formed by port 36 and opening 44.

Figures 4, 5:
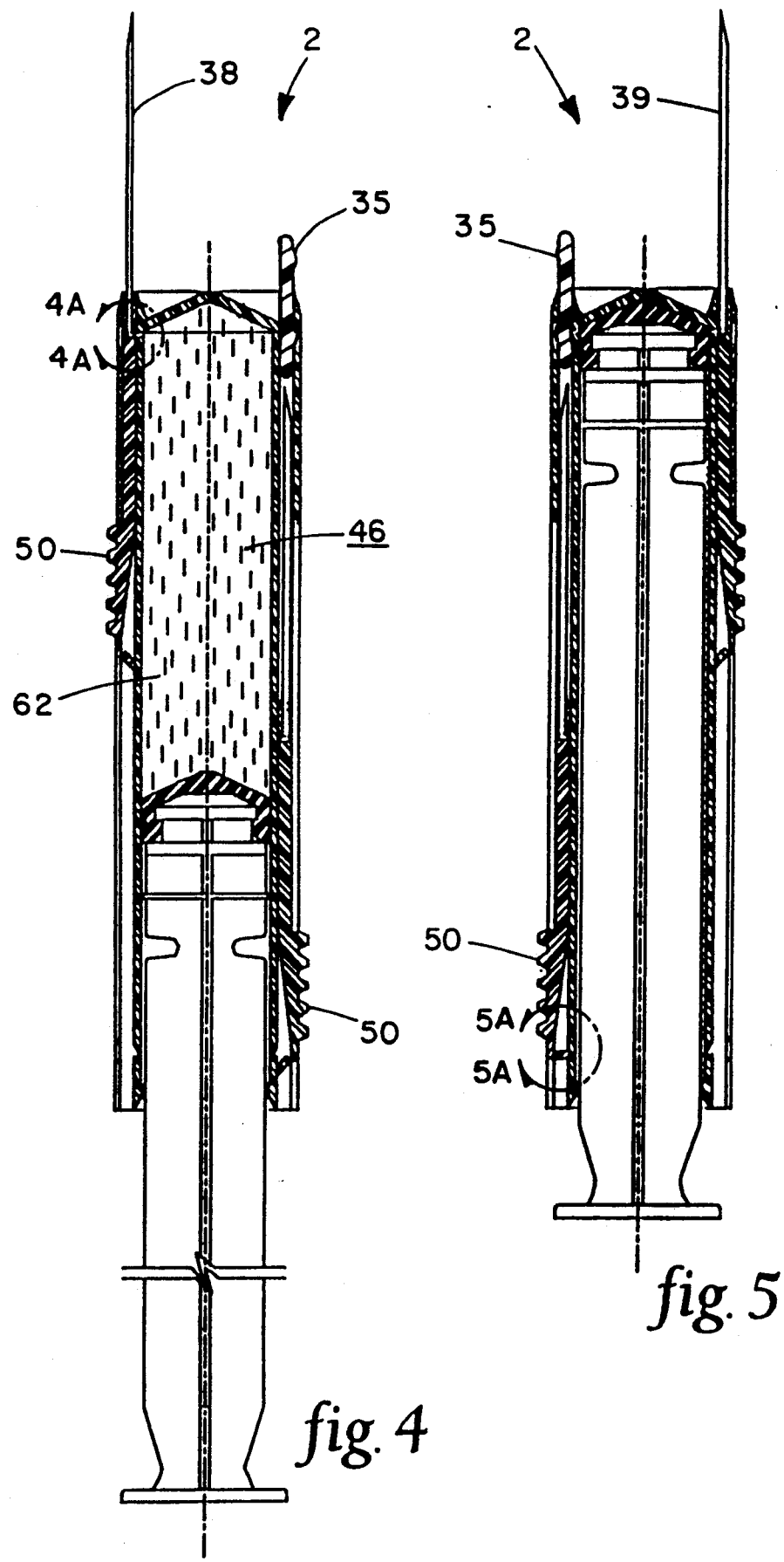
FIG. 4 is a front elevation cross-sectional view with the plunger retracted in the barrel and a first needle in the extended, use position after having aspirated a liquid pharmaceutical through the first needle and into the barrel.
FIG. 5 is a front elevation cross-sectional view with the first needle locked into a post-use, locked and retracted position, second needle in the extended, use position and the plunger fully inserted into the barrel after injecting the liquid pharmaceutical from the barrel and through the second needle.
Figure 4A:
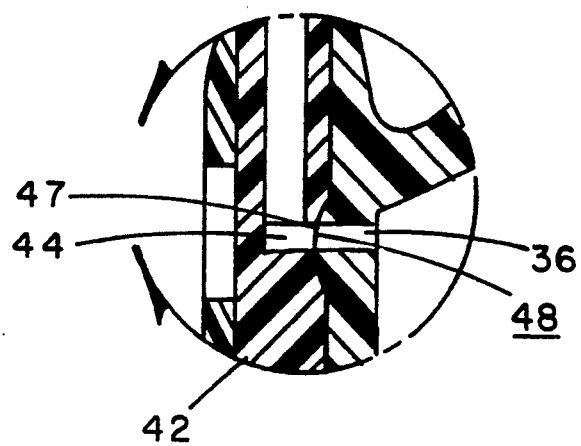
FIG. 4A is an enlarged view taken from FIG. 4 along line 4A—4A showing part of a first flow path fluidly coupling the variable volume region within the barrel with the first needle.

At the top of each of guides 14, 15 is an aperture 37 through which needles 38, 39 extend when in the in-use extended position. FIG. 4 shows first needle 38 in the in-use position. A removable plug 35 is provided which fits into aperture 37 (FIGS. 2–4). Use of plug 35 is described below.

Each needle mount 42 also includes a serrated end 50 which extends through slot 24. Serrated end 50 allows the user to move needle assembly 22 between the retracted and extended positions. To temporarily secure needle assembly 22 in the retracted and extended positions of FIGS. 3 and 4, serrated end 50 includes an extended width portion 52 sized to engage cutouts 30, 32 when needle assembly 22 is at the retracted and extended positions. As can be seen in FIGS. 1 & 3, serrated end 50 is naturally positioned in its radially outward position of FIGS. 1 & 3 so that serrated end 50 must be biased inwardly, that is towards axis 18, to disengage extended width portion 52 from cutouts 30, 32 before needle assembly 22 can be moved along interior 20 of guide 14. This keeps the needles 38, 39 from inadvertently moving from the safe, pre-use, retracted position of FIG. 3 or from the in-use, extended, and potentially hazardous, position of FIG. 4.

Figure 5A:
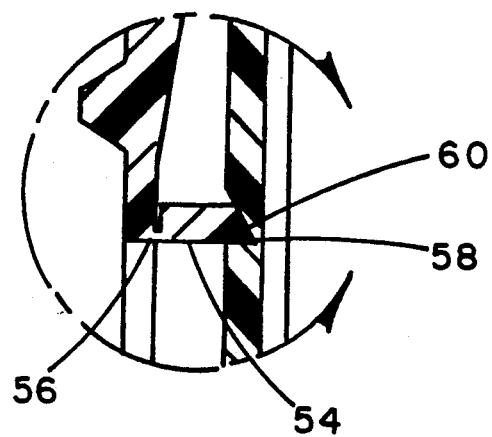
FIG. 5A is an enlarged view showing the locking tab at one end of the first needle mount engaging a recess stop formed in the barrel to prevent radially inward movement of the needle mount, thus locking the first needle assembly in the post-use, locked and retracted position.

As can be seen in FIG. 3, each needle mount 42 includes a tab 54 extending from extended width portion 52 at a hinge 56. Tab 54 has a bevelled end 58 which, due to its inclination in the pre-use, retracted position of FIG. 3, easily passes over a recess stop 60 formed in barrel 4 directly beneath cutout 30. The normal angular inclination of tab 54 in the pre-use, retracted position permits unimpeded movement of extended width portion 52 inwardly to allow portion 52 to disengage from cutout 30 in the pre-use, retracted position of FIG. 3 as well as from cutout 32 in the in-use, extended position. However, the configuration and orientation of tab 54 causes tab 54 to engage recessed stop 60 when moved from the in-use, extended position to the post-use, retracted and irreversibly locked position. This locking is illustrated best in FIG. 5A. As can be seen, radially inward movement of extended width portion 52 is prevented by the engagement of tab 54 within recessed stop 60. This prevents the disengagement of extended width portion 52 from cut-out 30, thus irreversibly locking first needle 38 in the retracted position of FIG. 5.

Syringe 2 is preferably provided so that both needle assemblies 22, 23 are in the pre-use, retracted position of FIG. 3 and packed in a sterile packaging or wrapping. Just prior to use, syringe 2 is removed from the packaging or wrapping. Plug 35 is removed from the aperture 37 overlying the first needle 38 so that first needle 38 can be extended. The first needle assembly 22 having the first needle 38 is then moved from the position of FIG. 3 to the position of FIG. 4 by pressing on serrated end 50 to disengage extended width portion 52 from cutout 30 until serrated end 50 reaches the end of slot 24. Releasing serrated end 50 permits portion 52 to engage cutout 32 to temporarily lock needle assembly 20 in the extended position of FIG. 4. Plug 35 is then positioned in aperture 37 overlying second needle 39. Plug 35 blocks port 36 adjacent second needle 39 so that air is not drawn into variable volume region 46 when a liquid 62 is drawn into variable volume region 46 through first needle 38.

The tip of first needle 38 is then used to pierce a vial membrane (not shown) and inserted into the liquid 62 to be injected. Plunger 6 is retracted to draw liquid 62 into the variable volume region 46 as illustrated in FIG. 4.

After drawing in the desired quantity of liquid 62 into variable volume region 46, first needle 38 is retracted since it may have been dulled when used to pierce the vial membrane. Second needle 39 is used for the injection as described below. To retract the first needle 38, the user presses on serrated end 50 to disengage portion 52 from cutout 32 and then draws first needle assembly 22 to the post-use, retracted and irreversibly locked position of FIG. 5. In doing so, tab 54 engages recessed stop 60, thus forcing portion 52 into cutout 30 to irreversibly lock first needle assembly 22 in the safe, post-use, retracted and locked position.

Plug 35 is then moved from the aperture 37 overlying second needle 39 and moved into the aperture 37 overlying first needle 38. As shown in FIG. 3, plug 35 has a shape which conforms to abutting surface 48 thereby providing an effective fluid plug for port 36. Plug 35 must be replaced before the injection otherwise liquid 62 may leak out of port 36 adjacent first needle 38 during the injection.

Second needle 39 is then extended in the above described manner for injecting liquid 62. Once second needle 39 is extended to the position shown in FIG. 5, the injection is given by depressing the plunger 6 thereby reducing the volume of the variable volume region 46 and forcing liquid 62 through second flow path 47. Once again, the second flow path is defined by the variable volume region 46, adjoining port 36, opening 44, and second needle 39. After the injection, second needle 39 is retracted and locked in the manner described above for safe disposal.

Modification and variation can be made to disclosed embodiment without departing from the subject of the invention as defined in the following claims. For example, the needle assembly and needle assembly guide could be modified to be a removable assembly for mounting to a conventional syringe structure having a conventional twist lock tip. The invention could also be practiced using packaged pharmaceutical containers of the type having a septum at one end and a piston at the other. A protective sheath may be used to cover the needle and temporarily the seal port. Two plugs 35 may be provided so that the apertures 37 overlying both ports can be plugged.

What is claimed is:

1. A dual needle safety syringe comprising:
   a barrel including a variable volume region;
   first and second needles each mounted to the barrel for movement between extended, use positions and retracted, non-use positions, the first and second needles also having first and second inlets and outlets, respectively;
   a first fluid path formed between the variable volume region and the first inlet when the first needle is in the extended, use position;
   a second fluid path formed between the variable volume region and the second inlet when the second needle is in the extended, use position; and
   means for reducing the volume of the variable volume region so that a fluid contained in the variable volume region is forced through at least one of said first and second flow paths, said first and second inlets, and said first and second outlets when at least one of the first and second needles is in the extended, use position.

2. The syringe structure of claim 1 wherein:
   the barrel having an interior, an exterior, an open proximal end and a distal end; and
   the volume reducing means comprises a plunger slidably mounted within the interior of the barrel, and extending from the proximal end.

3. The syringe of claim 1, wherein:
   the first and second needles are part of first and second needle assemblies, respectively, each needle assembly including a needle mount.

4. The syringe structure of claim 3 wherein the needle mount includes a portion which is movable.

5. The syringe of claim 1, further comprising:
   first and second needle assembly guides associated with an exterior of the barrel, the first and second needle assembly guides each having a needle assembly path along which a respective one of the first and second needle assemblies can move between the extended positions, with the first and second needles exposed, and the retracted positions, with the first and second needles housed within the first and second needle assembly guides respectively.

6. The syringe structure of claim 5 wherein each of the needle assembly guides is secured directly to the exterior of the barrel.

7. The syringe structure of claim 5 wherein each needle assembly guide is a one-piece extension of the barrel.

8. The syringe structure of claim 5 wherein:
   the first and second needles are part of first and second needle assemblies, respectively, each needle assembly including a needle mount; and
   each of the first and second needle assembly guides includes first and second catches configured to engage the movable portion of the needle mount when the needle assembly is at the extended and retracted positions to temporarily secure the needle assembly at said positions.

9. The syringe structure of claim 5 further comprising means for irreversibly locking at least one of the needle assemblies in the retracted position.

10. The syringe structure of claim 8 further comprising a tab pivotally secured to the movable portion and means for engaging the tab as the needle assembly is moved in a direction from the extended position to the retracted position to keep the movable portion engaged with the second catch thus irreversibly locking the needle assembly at the retracted position.

11. An improved syringe structure of the type including a barrel having a bore with a plunger slidably mounted therein, the improvement comprising:
    first and second hollow needles;
    means for mounting each of the needles at the outside of the barrel for movement along paths parallel to but radially offset from the axis of the bore, between an extended position, at which at least a portion of the needle is exposed, and a retracted position, at which the needle is enclosed within the mounting means, the mounting means including means for temporarily securing the needle assembly in the extended and retracted positions;
    first means for fluidly coupling the barrel bore with the first needle when the first needle is in the extended position; and
    second means for fluidly coupling the barrel bore with the second needle when the second needle is in the extended position.

12. The syringe structure of claim 11 wherein the mounting means includes:
    a deflectable member which secures the needle in the extended and retracted positions; and
    means for preventing a deflection of the deflectable member when the needle moves to the retracted position from the extended position so to irreversibly lock the needle in the retracted position.

13. A dual needle safety syringe comprising:
    a barrel having an interior, an exterior, an open proximal end, a distal end, and a variable volume region;

first and second needle assemblies including first and second hollow needles, respectively, each needle assembly including a needle mount having a portion which is movable;

first and second needle assembly guides integral with the exterior of the barrel and housing the first and second needle assemblies, respectively, the first and second needle assembly guides having a needle assembly path along which the needle assembly can move between an extended position, with the needle exposed, and a retracted position, with the needle housed within the needle assembly guide, each of the needle assembly guides including first and second catches configured to engage the movable portion of the needle mount when the needle assembly is at the extended and retracted positions to temporarily secure the needle assembly at said positions;

a first fluid path formed between the variable volume region and the first inlet when the first needle is in the extended, use position;

a second fluid path formed between the variable volume region and the second inlet when the second needle is in the extended, use position;

a plunger slidably mounted within the variable volume region and extending from the proximal end; and a tab pivotally secured to each of the movable portions of the needle mounts and means for engaging each of the tabs as the needle assembly is moved in a direction from the extended position to the retracted position to keep the movable portion engaged with the second catch thus irreversibly locking the needle assembly at the retracted position.

* * * * *